United States Patent [19]

Cardis

[11] Patent Number: 4,814,097

[45] Date of Patent: Mar. 21, 1989

[54] REACTION PRODUCTS OF DIALKYL PHOSPHITES WITH ELEMENTAL SULFUR, ALKYLENE OXIDE COMPOSITIONS CONTAINING SAME, AND THEIR USE IN LUBRICANT COMPOSITIONS

[75] Inventor: Angeline B. Cardis, Florence, N.J.

[73] Assignee: Mobile Oil Corporation, New York, N.Y.

[21] Appl. No.: 185,303

[22] Filed: Apr. 20, 1988

Related U.S. Application Data

[63] Continuation of Ser. No. 129,633, Dec. 7, 1987, abandoned, which is a continuation-in-part of Ser. No. 883,665, Jul. 8, 1986, Pat. No. 4,717,491.

[51] Int. Cl.[4] .......................................... C10M 137/02
[52] U.S. Cl. .................................. 252/46.6; 252/46.7; 568/14
[58] Field of Search ................. 252/46.6, 46.7; 568/14

[56] References Cited

U.S. PATENT DOCUMENTS

| | | | |
|---|---|---|---|
| 3,984,448 | 10/1976 | Lippsmeier | 260/429 R |
| 4,152,275 | 5/1979 | Horodysky et al. | 252/46.6 |
| 4,207,195 | 6/1980 | Horodysky | 252/46.6 |
| 4,212,753 | 7/1980 | Horodysky | 252/46.6 |
| 4,242,511 | 12/1980 | Grosse | 544/110 |
| 4,554,085 | 11/1985 | Zinbo et al. | 252/46.6 |
| 4,704,218 | 11/1987 | Horodysky et al. | 252/46.6 |
| 4,717,491 | 1/1988 | Cardis | 252/46.7 |

*Primary Examiner*—Jacqueline V. Howard
*Attorney, Agent, or Firm*—Alexander J. McKillop; Charles J. Speciale; Van D. Harrison, Jr.

[57] ABSTRACT

Dialkyl phosphites are reacted with sulfur. The resulting product is further reacted with an alkylene oxide to form a lube oil product. A better additive results when phosphorus pentoxide is then reacted with the resulting product and this product is further reacted with an amine to form an amine phosphate salt.

34 Claims, No Drawings

REACTION PRODUCTS OF DIALKYL PHOSPHITES WITH ELEMENTAL SULFUR, ALKYLENE OXIDE COMPOSITIONS CONTAINING SAME, AND THEIR USE IN LUBRICANT COMPOSITIONS

This is a continuation of application Ser. No. 129,633, filed on Dec. 7, 1987, now abandoned, which is a continuation-in-part of copending application Ser. No. 883,665 filed July 8, 1986, U.S. Pat. No. 4,717,491 which is incorporated herein by reference.

NATURE OF THE INVENTION

This invention relates to reaction products of dialkyl phosphites with elemental sulfur, reaction of the resulting product with epoxides, phosphorus pentoxide, and amines, and use of these products in lubricating oil formulations.

PRIOR ART

U.S. Pat. No. 3,984,448 discloses the use of metal oxides, such as those of copper, calcium, barium, magnesium, zinc, cadmium, titanium or lead in conjunction with elemental sulfur and O,O-dialkylphosphorus acid esters to produce dialkyl thiophosphates.

U.S. Pat. No. 4,242,511 discloses the reaction of O,S-dialkylthiophosphoric acid esters by subjecting a thiophosphate to partial dealkylation in forming the salt of the dealkylated product by treatment with an amine.

Although dithiophosphate products are known lubricant additives, their preparation involves processes resulting in noxious, undesirable by-products such as hydrogen sulfide and chloride-containing waste streams. Accordingly a primary object of this invention is to provide a process for preparing thiophosphate products which eliminates the production of the aforementioned undesirable by-products.

SUMMARY OF THE INVENTION

In brief, this invention comprises in one aspect reacting dialkyl phosphites with elemental sulfur to provide an intermediate reactive product and then further reacting this intermediate product with epoxides, olefins, or amines to obtain a desired lube oil additive. In another aspect this invention comprises reacting the product thus obtained with phosphorus pentoxide, followed by reaction with an amine, to obtain a second improved lube oil additive. This invention also comprises a method for preparing lube oils wherein the aforedescribed additives are added to a selected lubricating oil. This invention further comprises the resulting lube oil product.

DESCRIPTION OF THE INVENTION

In the present invention an intermediate reaction product is obtained by reacting dialkyl phosphites of the general formula

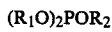

(R$_1$O)$_2$POR$_2$ where R$_1$ is a hydrocarbon radical of 4 to 18 carbon atoms and R$_2$ is hydrogen with elemental sulfur in the absence of any added catalyst in the presence of pulverulent sulfur at elevated temperature. Useful dialkyl phosphites include oleyl, phenyl, nonyl phenyl, octylphenyl, 2-ethyl hexyl, 1,3-dimethylbutyl, tridecyl, isodecyl, octyl and butyl, and mixed phosphites of the above radicals. If desirable, an unreactive organic solvent can be utilized. Preferably the organic solvent is selected from benzene, toluene, xylene, and mixed alkyl and aromatic petroleum distillates.

The pulverulent sulfur should conveniently have a mean particle size of less than one millimeter, preferably less than 0.01 millimeters, as this enables the reaction to be shortened. Reaction temperatures between 75° and 120° C. are preferred and a mole ratio of sulfur to phosphite of 0.8 to 1.2 is preferred. The reaction is carried out, preferably under a blanket of material such as nitrogen or other non-reactive gas. At the end of the reaction period the reaction mixture is allowed to cool to room temperature. The desired thiophosphate product is then stripped under vacuum to remove solvent and volatile byproducts and can be subsequently filtered or decanted from the reaction vessel, or optionally the reaction product of the first step may be further reacted without any purification.

This intermediate reaction product thus obtained is then further reacted with an amine, olefin, or alkylene oxide. The mole ratio of one of these reactants reacted with one mole of thiophosphate in the reaction product is 0.6 to 1.5. This second reaction is effected by mixing the reactants and allowing them to react (with added heat, if desirable) at a temperature between about 10° C. and about 90° C. The final product obtained can then be separated and purified by filtration and decantation. This product is then suitable for use in lube oil and grease formulations.

The amine compound to be reacted with the product formed by the alkyl phosphite and sulfur can be primary, secondary, tertiary or heterocyclic and can include various alkoxylated amines. Preferred amines include Primene 81R, benzotriazole, tolutriazole, the various tradenamed Ethomenes and Armenes such as Armene 2C and Ethomene C12, amine-containing polymeric succinimides, and aromatic amines such as dialkyl diphenylamine and (alkylated) phenyl naphthylamines. Primene 81R is the tradename for a mixture of tertiary-alkyl amines having an average number of carbon atoms per molecule of 11 to 13. Armene 2C is primarily dicocoamine, i.e., (C$_{12}$H$_{25}$)$_2$NH. Ethomene C12 is primarily bis(2-hydroxyethyl)cocoamine. Ethomene 2T is primarily di-tallow amine.

If olefins are to be utilized they can be selected from vinyl ethers, esters and amides and other such activated olefins.

Useful alkylene oxides include ethylene oxide, propylene oxide and butylene oxide, as well as C$_{12}$ to C$_{24}$ alpha olefin epoxides.

As indicated previously, although the product obtained is useful as a lube oil additive certain of the products, particularly those formed by reaction of the phosphite-sulfur product with alkylene oxides, provide a product of improved performance if further reacted with phosphorus pentoxide, P$_2$O$_5$ in a mole ratio of about 1 mole of P$_2$O$_5$ to about 3 moles of thiophosphate product. The acid phosphate so formed is then further reacted with an amine in an amount necessary to neutralize the acidity or optionally, the product may be over-based or under-neutralized as desired. The amines suitable for this purpose include primary, secondary, tertiary or heterocyclic, and can include various alkoxylated amines. Preferred amines include Primene 81R, benzotriazole, tolutriazole, the various ethomenes and armenes such as Armene 2C and Ethomene C12, amine-containing polymeric succinimides, and aromatic amines such as dialkyl diphenylamine and (alkylated) phenyl naphthylamines.

The resulting reaction products of this invention are used with lubricating oils or greases to the extent of from about 0.1% to about 10% by weight of the total composition. Furthermore, other additives, such as detergents, antioxidants, antiwear agents and the like may be present. These can include phenates, sulfonates, succinimides, zinc dialkyl dithiophosphates, polymers, calcium and magnesium salts of phenates and sulfonates, including overbased salts of the same, and the like.

The lubricants contemplated for use with the esters herein disclosed include mineral and synthetic hydrocarbon oils of lubricating viscosity, mixtures of minerals oils and synthetic oils and greases from any of these, including the mixtures. The synthetic hydrocarbon oils include long-chain alkanes such as cetanes and olefin polymers such as oligomers of hexene, octene, decene, and dodecene, etc. These additives are especially effective in synthetic oils formulated using mixtures of synthetic hydrocarbon olefin oligomers and lesser amounts of hydrocarbyl carboxylate ester fluids. The other synthetic oils, which can be used alone with the compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

Having described the invention in general aspects, the following examples are offered as specific illustrations. Parts are by weight.

EXAMPLE 1

To 579 g (1.0 moles) dioleyl phosphite was added 32 g (1.0 moles) sulfur. The temperature was raised to 110° C. under a nitrogen atmosphere with stirring and held for eight hours.

The reaction mixture was cooled to ambient temperature and then held in an ice bath as propylene oxide (87 g, 1.5 moles) was added over one and one-half hours. The temperature was increased to reflux the excess propylene oxide (pot temperature=90° C.). After two hours, the excess propylene oxide had distilled up the condenser. Heptane (100 cc) was added, and refluxing was continued an additional three hours. The solvent was distilled off and the product was vacuum topped at 20 mm Hg, 100° C.

The product was cooled to 50° C. and filtered through diatomaceous earth.

EXAMPLE 2

The product of Example 1 (669 g, 1.0 moles) was stirred at 50° C. under nitrogen as phosphorus pentoxide (47 g, 0.33 moles) was added in portions over forty-five minutes. The temperature was raised to 75° C. and held two and one-half hours. The product was then filtered.

The recovered filtrate, the product, was stirred at 50° C. as Primene 81R (105 g) was added dropwise over twenty minutes. Primene 81R is a mixed $C_{12}$ to $C_{14}$ tertiary alkyl primary amine produced and sold commercially by Rohm and Haas Co. This final product was stirred an additional hour at 50° C.

Following the procedures of Examples 1 and 2, products were prepared from dilaurylhydrogen phosphite, bis-2-ethylhexylhydrogen phosphite, and dibutylhydrogen phosphite.

EXAMPLE 3

Sulfur (32 g, 1.0 mole) and bis-(2-ethylhexyl) hydrogen phosphite (306 g, 1.0 mole) were stirred under nitrogen as the temperature was increased from ambient to 100° C. At 100° C., Primene 81R (191 grams) was added dropwise over twenty minutes. After the addition, stirring was continued an additional hour at 100° C. The temperature was reduced to 50° C. and the product was filtered through diatomaceous earth.

Following the procedure of Example 3, products were also made from dibutylhydrogen phosphite, dioleylhydrogen phosphite, and dilaurylhydrogen phosphite.

EVALUATION OF PRODUCTS

The products described herein were blended in mineral oil and tested in the Shell Four-Ball Wear Test. The results in Table 1 demonstrate the antiwear protection afforded by these products. The mineral oil blends were further evaluated for EP properties in the Four-Ball Weld Test. The results are listed in Table 2.

TABLE 1

| FOUR BALL WEAR TEST SCAR DIAMETER (MM) ½ Inch Balls, 52100 Steel, 60 Kg., 30 Minutes, 1.5% | | | | |
|---|---|---|---|---|
| Example | R | Temp., °F. | 1000 RPM | 2000 RPM |
| Base Stock | | 200 | 1.5 | 2.0 |
| | | 390 | 1.8 | 1.9 |
| 1 | Butyl | 200 | 0.53 | 0.8 |
| | | 390 | 0.8 | 0.75 |
| 1 | 2-Ethylhexyl | 200 | 0.55 | 0.5 |
| | | 390 | 1.6 | 1.6 |
| 1 | Lauryl | 200 | 0.55 | 0.5 |
| | | 390 | 1.4 | 1.9 |
| 1 | Oleyl | 200 | 0.6 | 1.6 |
| | | 390 | 1.4 | 1.7 |
| 2 | Butyl | 200 | 0.5 | 0.7 |
| | | 390 | 1.2 | 1.7 |
| 2 | 2-Ethylhexyl | 200 | | |
| | | 390 | | |
| 2 | Lauryl | 200 | | |
| | | 390 | | |
| 2 | Oleyl | 200 | 0.5 | 0.8 |
| | | 390 | 1.7 | 1.8 |
| 3 | Butyl | 200 | 0.5 | 0.5 |
| | | 390 | 1.1 | 1.8 |
| 3 | 2-Ethylhexyl | 200 | 0.55 | 0.75 |
| | | 390 | 0.55 | 1.75 |
| 3 | Lauryl | 200 | 0.5 | 1.5 |
| | | 390 | 0.8 | 1.7 |
| 3 | Oleyl | 200 | 0.4 | 0.6 |
| | | 390 | 1.4 | 1.7 |

TABLE 2

| FOUR-BALL WELD, 1.5% ADDITIVE CONCENTRATION | | | |
|---|---|---|---|
| Example | R | Weld Load (Kg) | Mean Hertz Load |
| Base Stock | | 126 | 26.9 |
| 1 | Butyl | 200 | 46.6 |
| 1 | 2-Ethylhexyl | 160 | 37.1 |
| 1 | Lauryl | 160 | 34.4 |
| 1 | Oleyl | 160 | 41.1 |
| 2 | Butyl | 200 | 40.9 |
| 2 | 2-Ethylhexyl | | |
| 2 | Lauryl | | |

TABLE 2-continued

| FOUR-BALL WELD, 1.5% ADDITIVE CONCENTRATION | | | |
|---|---|---|---|
| Example | R | Weld Load (Kg) | Mean Hertz Load |
| 2 | Oleyl | 200 | 40.6 |
| 3 | Butyl | 200 | 46.3 |
| 3 | 2-Ethylhexyl | 200 | 43.6 |
| 3 | Lauryl | 200 | 48.4 |
| 3 | Oleyl | 200 | 41.2 |

The product of Example 2, in which R is oleyl, was blended into a fully formulated hydraulic oil at a concentration of 0.2 weight percent and evaluated in the ASTM D2882 wear test in comparison with a similarly formulated hydraulic oil containing 0.7 weight percent of a commercially available zinc dithiophosphate. The results are listed in Table 3.

TABLE 3

| Hydraulic oil Containing | Concentration, Weight Percent | ASTM D2882 Wear, Mgrams |
|---|---|---|
| ZnDTP | 0.7 | 28 |
| Ex.2, R is oleyl | 0.2 | 13 |

What is claimed is:

1. A process for making a reaction product suitable for use as an additive in lubricating oils comprising
   (a) reacting a dialkyl phosphite with elemental sulfur in a mole ratio of sulfur to phosphite of between 0.8 and about 1.2 at a temperature between about 75° C. and about 120° C. and in the absence of any catalytic material added to promote reaction of the two reactants;
   (b) separating the reaction product thereby obtained;
   (c) reacting the reaction product from (b) with an alkylene oxide in a mole ratio of alkylene oxide to phosphite of about 0.9 to about 1.2, at a temperature of between about 10° C. and about 90° C.; and
   (d) separating from the resulting reaction mixture the desired product.

2. A process for making a reaction product suitable for use as an additive in lubricating oils comprising
   (a) reacting a dialkyl phosphite with elemental sulfur in a mole ratio of sulfur to phosphite of between 0.8 and about 1.2 at a temperature between about 75° C. and about 120° C. and in the absence of any catalytic material added to promote reaction of the two reactants;
   (b) reacting the reaction product from (a) with an alkylene oxide in a mole ratio of alkylene oxide to phosphite of about 0.9 to about 1.2, at a temperature of between about 10° C. and about 90° C.; and
   (c) separating from the resulting reaction mixture the desired product.

3. The process of claim 2 wherein said phosphite has the structural formula $(R_1O)_2POH$ where $R_1$ is an alkyl hydrocarbon radical of 4 to 18 carbon atoms.

4. The process of claim 1 wherein the dialkyl phosphite is selected from the group consisting of oleyl, phenyl, nonylphenyl, octylphenyl, 2-ethyl hexyl, 1,3-dimethyl butyl, tridecyl, isodecyl, octyl, butyl, and mixed phosphites.

5. The reaction product produced by the process of claim 2.

6. The reaction product produced by the process of claim 3.

7. The reaction product produced by the process of claim 4.

8. A lubricant composition comprising a lubricant and between about 0.1% and about 10% by weight of the total composition of the reaction product produced by the process of claim 2.

9. A lubricant composition comprising a lubricant and between about 0.1% and about 10% by weight of the total composition of the reaction product produced by the process of claim 3.

10. A lubricant composition comprising a lubricant and between about 0.1% and about 10% by weight of the total composition of the reaction product produced by the process of claim 4.

11. A process for making a reaction product suitable for use as an additive in lubricating oils comprising
   (a) reacting a dialkyl phosphite with elemental sulfur in a mole ratio of sulfur to phosphite of between 0.8 and about 1.2 at a temperature between about 75° C. and about 120° C. and in the absence of any catalytic material added to promote reaction of the two reactants;
   (b) separating the reaction product thereby obtained;
   (c) reacting the reaction product from (b) with an alkylene oxide in a mole ratio of alkylene oxide to phosphite of about 0.9 to about 1.2, at a temperature of between about 10° C. and about 90° C;
   (d) separating the reaction product obtained in (c), and reacting about 3 moles of it with about 1 mole of $P_2O_5$;
   (e) separating from the resulting reaction mixture the desired product; and
   (f) reacting the product obtained in (e) with an amine in a ratio by weight of between about 7 and about 25 parts of amine to 100 parts of the reaction product of (e).

12. A process for making a reaction product suitable for use as an additive in lubricating oils comprising
   (a) reacting a dialkyl phosphite with elemental sulfur in a mole ratio of sulfur to phosphite of between 0.8 and about 1.2 at a temperature between about 75° C. and about 120° C. and in the absence of any catalytic material added to promote reaction of the two reactants;
   (b) reacting the reaction product from (a) with an alkylene oxide in a mole ratio of alkylene oxide to phosphite of about 0.9 to about 1.2, at a temperature of between about 10° C. and about 90° C.;
   (c) reacting about 3 moles of the reaction product obtained in (b) with about 1 mole of $P_2O_5$;
   (d) separating from the resulting reaction mixture the desired product; and
   (e) reacting the product obtained in (d) with an amine in a ratio by weight of between about 7 and about 25 parts of amine to 100 parts of the reaction product of (d).

13. The process of claim 12 wherein said phosphite has the structural formula $(R_1O)_2POH$ where $R_1$ is an alkyl hydrocarbon radical of 4 to 18 carbon atoms.

14. The process of claim 12 wherein the dialkyl phosphite is selected from the group consisting of oleyl, phenyl, nonylphenyl, octylphenyl, 2-ethyl hexyl, 1,3-dimethyl butyl, tridecyl, isodecyl, octyl, butyl, and mixed phosphites.

15. The process of claim 12 wherein said amine is selected from the group consisting of primary, secondary, tertiary, heterocyclic and aromatic amines.

16. The process of claim 12 whrein said amine is one or a mixture of alkoxylated amines of between about 4 and about 30 carbon atoms.

17. The process of claim 12 wherein said amine is selected from the group consisting of benzotriazole; tolutriazole, amine-containing polymeric succinimides, dialkyldiphenyl amine and alkylated phenyl naphthylamines.

18. The process of claim 12 wherein said amine is selected from the group consisting of Primene 81R, Armene 2C, Ethomene C12, Ethomene 2T, and Armene O.

19. The reaction product produced by the process of claim 12.

20. The reaction product produced by the process of claim 13.

21. The reaction product produced by the process of claim 14.

22. The reaction product produced by the process of claim 15.

23. The reaction product produced by the process of claim 16.

24. The reaction product produced by the process of claim 17.

25. The reaction product produced by the process of claim 18.

26. A lubricant composition comprising a lubricant and between about 0.1% and about 10% by weight of the total composition of the reaction product produced by the process of claim 12.

27. A lubricant composition comprising a lubricant and between about 0.1% and about 10% by weight of the total composition of the reaction product produced by the process of claim 13.

28. A lubricant composition comprising a lubricant and between about 0.1% and about 10% by weight of the total composition of the reaction product produced by the process of claim 14.

29. A lubricant composition comprising a lubricant and between about 0.1% and about 10% by weight of the total composition of the reaction product produced by the process of claim 15.

30. A lubricant composition comprising a lubricant and between about 0.1% and about 10% by weight of the total composition of the reaction product produced by the process of claim 16.

31. A lubricant composition comprising a lubricant and between about 0.1% and about 10% by weight of the total composition of the reaction product produced by the process of claim 17.

32. A lubricant composition comprising a lubricant and between about 0.1% and about 10% by weight of the total composition of the reaction product produced by the process of claim 18.

33. The reaction product produced by the process of claim 2.

34. A lubricant composition comprising a lubricant and between about 0.1% and about 10% by weight of the total composition of the reaction product produced by the process of claim 2.

* * * * *